(12) United States Patent
Gimenez et al.

(10) Patent No.: US 9,662,067 B2
(45) Date of Patent: May 30, 2017

(54) SYSTEM FOR SENSING LIGHT EXPOSURE OF A USER

(71) Applicant: PHILIPS LIGHTING HOLDING B.V., Eindhoven (NL)

(72) Inventors: Marina Cecilia Gimenez, Groningen (NL); Lucas Josef Maria Schlangen, Eindhoven (NL)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 0 days.

(21) Appl. No.: 14/914,895

(22) PCT Filed: Aug. 26, 2014

(86) PCT No.: PCT/EP2014/068078
§ 371 (c)(1),
(2) Date: Feb. 26, 2016

(87) PCT Pub. No.: WO2015/028462
PCT Pub. Date: Mar. 5, 2015

(65) Prior Publication Data
US 2016/0199000 A1    Jul. 14, 2016

(30) Foreign Application Priority Data

Aug. 28, 2013   (EP) .................................... 13181934

(51) Int. Cl.
*H05B 37/02*   (2006.01)
*A61B 5/00*    (2006.01)
(Continued)

(52) U.S. Cl.
CPC .......... *A61B 5/4857* (2013.01); *A61B 5/0002* (2013.01); *A61B 5/1118* (2013.01);
(Continued)

(58) Field of Classification Search
CPC ...... A63B 2024/0068; A63B 2220/836; A63B 24/0062; A63B 2220/80; H04L 67/12;
(Continued)

(56) References Cited

U.S. PATENT DOCUMENTS 8,852,127 B2 *  10/2014  Bell ......................... A61B 5/11
                                                         340/573.1
2006/0224047 A1 *  10/2006  Suzuki .................. A61B 5/1118
                                                            600/300
(Continued)

FOREIGN PATENT DOCUMENTS

WO    2011089539 A1    7/2011

OTHER PUBLICATIONS

Van Laerhoven, Kristof, et al., "Sustained Logging and Discrimination of Sleep Postures With Low-Level, Wrist-Worn Sensors," Wearable Computers, 2008. ISWC 2008. 12th IEEE International Symposium on, IEEE, Sep. 28, 2008 (8 Pages).

*Primary Examiner* — Thai Pham
*Assistant Examiner* — Borna Alaeddini

(57) ABSTRACT

The invention relates to a system (100) for sensing ambient light intensity, comprising a wearable device (10) with at least one pair of light receivers (20, 22, 23, 24, 25) arranged in two different positions for receiving light from the two different directions, and a control unit (110) configured to determine a directional illuminance based on light intensities of the light received by the pair of light receivers (20, 22, 23, 24, 25).

11 Claims, 4 Drawing Sheets

(51) Int. Cl.
*G01J 1/02* (2006.01)
*G01J 1/16* (2006.01)
*G01J 1/42* (2006.01)
*G01J 1/04* (2006.01)
*A61B 5/11* (2006.01)
*A61N 5/06* (2006.01)

(52) U.S. Cl.
CPC ............ *A61B 5/742* (2013.01); *G01J 1/0219* (2013.01); *G01J 1/0228* (2013.01); *G01J 1/0233* (2013.01); *G01J 1/0271* (2013.01); *G01J 1/0488* (2013.01); *G01J 1/1626* (2013.01); *G01J 1/4204* (2013.01); *G01J 1/4228* (2013.01); *H05B 37/0281* (2013.01); *A61B 5/681* (2013.01); *A61B 2560/0242* (2013.01); *A61B 2560/0475* (2013.01); *A61N 2005/0628* (2013.01); *A61N 2005/0657* (2013.01); *G01J 2001/0261* (2013.01); *H05B 37/0218* (2013.01); *H05B 37/0227* (2013.01)

(58) Field of Classification Search
CPC .... A61B 5/681; A61B 5/02438; G01J 1/4204; H05B 37/0218; Y02B 20/46
See application file for complete search history.

(56) References Cited

U.S. PATENT DOCUMENTS

| | | |
|---|---|---|
| 2008/0319354 A1 | 12/2008 | Bell et al. |
| 2009/0177097 A1 | 7/2009 | Ma et al. |
| 2012/0330387 A1* | 12/2012 | Ferraz Rigo ......... A61N 5/0618 607/90 |
| 2013/0100097 A1 | 4/2013 | Martin |
| 2014/0107493 A1* | 4/2014 | Yuen .................... H04W 4/027 600/473 |
| 2014/0135631 A1* | 5/2014 | Brumback ......... A61B 5/02438 600/479 |
| 2014/0278229 A1* | 9/2014 | Hong .................. A61B 5/7455 702/160 |

* cited by examiner

SYSTEM FOR SENSING LIGHT EXPOSURE OF A USER

CROSS-REFERENCE TO PRIOR APPLICATIONS

This application is the U.S. National Phase application under 35 U.S.C. §371 of International Application No. PCT/EP2014/068078, filed on Aug. 26, 2014, which claims the benefit of European Patent Application No. 13181934.4, filed on Aug. 28, 2013. These applications are hereby incorporated by reference herein.

FIELD OF THE INVENTION

The invention relates to a system for sensing ambient light intensity, as well as to a corresponding method for sensing ambient light intensity using such a system. The system may be constituted by a wearable device for sensing ambient light intensity, or include such a wearable device.

BACKGROUND OF THE INVENTION

Exposure to light is the key mechanism that enables a proper synchronization of the body clock with the solar day cycle. Timing, duration, intensity and spectral composition of light exposure all have impact on the so-called entrainment of a person to a 24-hour circadian rhythm. In particular, light exposure on the eyes strongly controls the rest-activity pattern of a person. For certain people who have a phase shift of their internal body clock relative to the social schedules around them, exposure to bright light at well-defined times can be used to shift their body clock forward or backwards to better align it with their social needs. Also for the treatment of seasonal affective disorder, timed and regular exposure to bright light is an effective means. For biological, non-visual effects of light, especially the vertical illuminance at the eye position is of particular relevance. This vertical illuminance needs to exceed a certain threshold level for enough time a day in order to achieve a healthy, well-entrained and stable circadian rhythm.

Hence, the assessment of light levels, especially of vertical light levels, to which a person is exposed over the course of multiple days or even weeks is an important instrument for the diagnosis of human behavior and physical activity. To this end, existing actigraphic products measure activity and light exposure of a user. Most popular are wrist worn devices having an integrated light sensor, e.g. Actiwatches. However, these devices do not allow for an accurate measurement of the vertical ocular illuminance of a user, since they can measure light only in one direction, which usually does not coincide with the viewing direction of the eyes.

In present actigraphic devices, the light sensor module is usually mounted on a front surface such that the axis of main sensitivity is orthogonal to a display surface of the device, i.e. orthogonal to the outer hand surface of the user. Thus, the measurement direction depends on the position of the wrist and on the body posture, so that the axis of main sensitivity of the sensor is completely independent from the direction of gaze of the user. For instance, when people are standing with their arms pointing downwards, the device will measure vertical illuminance. However, when people are seated with their arms on the lap or desk, the device will measure light exposure in a rather horizontal orientation. Since for biological, non-visual effects of light it is important to evaluate the light exposure at the eye in the vertical direction, the current wrist worn devices do not give an optimal measure of the vertical ocular illuminance. It is estimated that their light measurements reflect less than 0.5 of the actual light exposure at eye level. Moreover, they do not take account for situations, such as sensor coverage or the like, where measurements of illuminance might not be possible due to coverage of the sensor by clothing (long sleeves).

Such a wrist-worn device is shown, for example, in US 2008/0319354 A1, showing a system and method for monitoring information related to sleep. The wrist-worn device shown in this document comprises an illumination sensor to provide information related to the intensity of ambient illumination of the user. The signal of the sensor can be further processed by suitable electronic computing means.

US 2013/0100097 A1 relates to a device and method of controlling lighting of a display based on ambient lighting conditions.

KRISTOF VAN LAERHOVEN ET AL., "Sustained logging and discrimination of sleep postures with low-level, wrist-worn sensors", WEARABLE COMPUTERS, 2008. ISWC 2008. 12$^{th}$ IEEE INTERNATIONAL SYMPOSIUM ON, IEEE, PISCATAWAY, N.J., USA, 28 Sep. 2008 (2008 Sep. 28), pages 69-76, relates to a study evaluating the use of simple low-power sensors for a long-term coarse grained detection of sleep postures.

WO 2011/089539 A1 relates to a control device, wearable device and lighting system for light therapy purposes.

In the following, directional illuminance is defined as luminous flux per area on a plane in this direction. For instance, vertical or horizontal illuminance refers to light falling on a vertical or horizontal surface, respectively.

SUMMARY OF THE INVENTION

It is therefore an object of the present invention to provide a system for sensing ambient light that is capable of accurate measurements of directional illuminance, i.e. illuminance in a certain direction, such as horizontal and/or vertical illuminance, and a method therefore.

This object is achieved by the features of the independent claims.

The invention is based on the idea to detect light using at least two light receiving means and to determine a vertical and/or horizontal illuminance of a user using the detected light data, such as intensity or spectrum. The light receiving means may be provided on at least one portable device, e.g. a wearable device to be worn by a user. Thus, a light exposure sensing system for sensing light exposure of a user may comprise at least one wearable device; at least two light receivers configured to receive light from different directions, the light receivers being arranged on the at least one wearable device, and a control unit configured to determine a directional illuminance based on light intensities of the light received by the at least two light receivers.

Hence, according to one embodiment, a system is provided having at least two light receiving means arranged on at least one body wearable device, such that light capturing areas or light receiving surfaces of the light receiving means have normals in different directions. Thus, a light receiving means with a vertical light receiving surface may measure vertical illuminance. Here, a main light receiving direction or light sensing direction of the light receiving means generally refers to the direction of main sensitivity of the light receiving means, which generally is the direction orthogonal to the light capturing area thereof. Preferably, one wearable device is provided including the light receiving means arranged in different orientations. But the system may also comprise two wearable devices or more, having each at least one light receiving means, for instance a head-worn device, a wrist-worn device, a broche-type device or the like. When using body worn devices, the orientation of the devices depends on the body posture of the user. Therefore, the wearable devices are preferably configured such that the light receiving directions of the light receiving means will differ in the most common body postures of the user wearing the devices. The light data corresponding to the light received by the light receiving means, i.e. corresponding to the different directions, are used by a control unit to determine a directional illuminance. Preferably, a vertical and/or horizontal illuminance of a user is determined. The light data may correspond to intensity and/or spectral data. Thus, the object can be achieved by a light exposure sensing system with a bi-directional light sensing function including at least one body wearable device, wherein light exposure measured in at least two different directions is combined by an algorithm to yield a measure for the horizontal and/or vertical illuminance of a user, e.g. using a ratio of light data provided from the light receivers.

According to the present invention, at least two light receiving means or light receivers may be arranged such that they have main light sensing directions independent from each other. Most preferred, the light receiving means are arranged orthogonally to each other. Thus, light from different directions, preferably from orthogonal directions, can be received and corresponding light data is then used to determine a (vertical) illuminance.

Further, a control unit may be provided in the light exposure sensing system of the present invention. This control unit may be configured to combine light data corresponding to light received by the light receivers, thus achieving a more precise measurement of the vertical and/or horizontal illuminance reaching the user's eye. By combining, e.g. comparing, averaging or taking the ratio, the readings of different light sensing directions, a light exposure parameter can be obtained that yields a better correlation with the vertical illuminance at the eye position, as compared to a device with a single light sensing direction. This correlation is even further improved, when combining light data corresponding to light received from orthogonal directions. The control unit may be included in the wearable device (or in one of the wearable devices). However, the light exposure sensing system may also include a separate control unit for determining the illuminance based on the received light. This separate control unit may be integrated in a docking station for charging and/or calibrating the wearable device. In any case, the control unit and the at least one wearable device may be configured to exchange data via wire based or wireless technologies.

Preferably, the light receivers are grouped in pairs, and the light receivers of each pair may be located such at the surface of one wearable device that light may be received from orthogonal directions. For instance, a first light receiver may be arranged at a front surface and a second light receiver at a side surface of the device. Possibly, the wearable device includes more than one pair of light receivers. In this case, at least one of the light receivers may be paired with more than one other light receiver arranged orthogonally thereto. As an example, the device may include four lateral light receivers arranged at lateral surfaces of the device and one front light receiver arranged at the front surface of the device. Thus, the front light receiver may be paired with one or more of the lateral light receivers. Preferably, the control unit is configured to define pairs based on a condition of orthogonality. There may also be additional conditions considered during setting up of pairs of light receivers, such as an orientation of the wearable device or whether a light intensity of light received by a light receiver exceeds a certain threshold. Thus, one preferred embodiment for a light exposure sensing system includes at least one wearable device with at least one pair of light receivers arranged in two different positions for receiving light from the two different directions, and a control unit configured to determine a vertical illuminance based on light intensities of the light received by the pair of light receivers.

Generally, the light receivers may be of the same type, or they may differ with respect to at least one of spectral or spatial sensitivity. Here, spectral sensitivity refers to the sensitivity of the light receiver for a spectral bandwidth. Spatial sensitivity refers to the angle with respect to the normal of the light receiving surface, within which light is received by the respective light receiver, i.e. to the directional sensitivity of the light receiver. The light receivers may be sensible for white light or light of at least of one predetermined spectral bandwidth. In other words, the light receivers may include a white light sensor and/or a RGB light sensor. In other words, the light receivers may be configured to receive light of one or a plurality of spectral ranges, for example within the visible light spectrum or also including the infrared or ultraviolet spectral range. Also, only light data corresponding to a predetermined wavelength band may be considered, e.g. only short wavelengths due to the higher spectral sensitivity of the circadian system in this range.

Even further, each light receiver may include a light sensor for generating a signal with light data corresponding to the received light. Alternatively, some or all of the light receivers may be connected via light guiding means to one common light sensor that generates a signal corresponding to the light received by the respective light receiver. In this case, the light receivers may not be provided as light sensors, but only as optical light collecting devices, such as optical lenses, coupled to light conducting fibers for supplying the collected light towards the sensor for further processing. Therefore, the wearable device may have only one light sensing element using optical fibers for guiding light from different directions to the light sensing element. Signals generated corresponding to the received light may be transmitted to the control unit for determining the illuminance.

The wearable or body wearable device may be integrable in clothing by some fixing mechanism, such as a press button or the like. In a preferred example, the wearable device is designed as a watch type device having a wristband for attaching the device to a user's wrist. Possibly, the device may be integrated in a wristwatch. The wearable device may comprise an operation module and a wristband connected to the operation module, wherein the light receivers may be arranged in different positions on the operation module and/or the wristband. Preferably, the operation module includes an integrated circuit for processing and storing signals provided by the light receivers. Other configurations for a wearable device are broche-type, belt-type or headlamp-type devices.

According to a preferred embodiment, the wearable device includes further an activity measuring unit for measuring body parameters of the user, such as, for instance, heart rate, body temperature, blood oxygen saturation etc. Preferably, the system includes further a storage unit for storing and logging data. The storage unit may be included in the control unit, or it may be provided separately. In the latter case or in case that the control unit is provided separately or in case that more than one wearable device is provided, at least one wearable device includes preferably a communication unit for data exchange, e.g. between wearable devices and/or other units of the system, or also between the wearable device and other systems. This communication may be wireless or wire-based. Thus, the light exposure sensing system may record data about light exposure of a user, preferably in addition to further data such as activity data, time, orientation and the like. In addition, the wearable device may include a display unit for displaying measured parameters, time or the like.

Furthermore, an orientation unit may be integrated in the wearable device for determining an orientation thereof. By these means, the control unit may weight the received light data, e.g. intensity or spectral data, from the light receivers based on the orientation of the respective light receiver with respect to ground. Such an orientation unit may include a 3D motion sensing device and/or an accelerometer. For instance, only vertical illuminance may be considered for determining the eye illuminance of a user. Thus, only when the light receiver is oriented vertically, i.e. having a light receiving surface in vertical direction, the illuminance is sampled from this receiver, neglecting light data for non-vertical light receiver orientations.

In one exemplary embodiment, the light exposure sensing system may be combined with a lighting control system, so that a central control unit of the lighting control system uses the determined illuminance values received from the light exposure sensing system as control parameters or feedback parameters to control a lighting system. The lighting system may include a plurality of lighting devices or a single device like a lamp, a goLITE or energy light. By these means, an appropriate light exposure of a user over a certain time can be ensured.

Preferably, determining the directional illuminance, in particular the vertical illuminance, includes taking a ratio of light data corresponding to light received by the two light receivers, and in particular taking a ratio of the light intensities. Since the light receivers are oriented towards different directions, the ratio may be based on light of different directions. By these means, several parameters may be assessed, such as the vertical illuminance, a contribution of daylight to the overall illuminance, an orientation of the device and/or a situation of receiver coverage, in which one or more of the light receivers are covered, so that less light is received.

In a further embodiment, the determination of the illuminance includes averaging the light data of at least two different directions (preferably orthogonal directions). By these means, a light exposure parameter may be obtained that yields a better correlation with the illuminance at the eye position, e.g. the vertical illuminance, as compared to a device with a single light sensing direction. Since preferably, the light receivers are arranged in orthogonal directions, also the averaged signals or light intensities may correspond to two different orthogonal light sensing directions. This averaging may also refer to weighted averaging, wherein the signals are first weighted and the average is taken from the weighted signals. That is, averaging may be done using different weighting factors for the receiver contributions. The weighting factor may depend on the orientation of the device (the orientation may be derived e.g. by a 3D accelerometer in the device or be determined based on the light intensities of light received from the different directions of the light receivers), or on the absolute intensities of the receivers and/or on their ratio. The weighting factor for one sensor signal may be zero, so that one signal is neglected, as described below.

Generally, the light data, e.g. light intensities, may be weighted when determining the illuminance. Preferably, the light data are weighted based on an orientation of the wearable device, and thus based on an orientation of the corresponding light receivers. For instance, the light intensity of the light receiver being closer to a vertical direction, i.e. measuring vertical illuminance, may be weighted stronger than that of the other light receiver, when combining the light intensities for determining the illuminance. After weighting, a weighted average of the light intensities may be determined.

Under predefined conditions, only one of the light intensities received by the light receivers may be considered for determining the illuminance. For instance, in the situation of receiver coverage, only the light data of the light receiver having the higher value may be considered, i.e. after comparing the received light intensities for determining the higher intensity thereof. In another example, only the light intensity corresponding to the light receiver(s) closer to a vertical orientation may be considered. The more vertical light receiver(s) may also be determined by comparing the received light intensities, as described herein. Alternatively to considering only one signal of the light receivers, all signals may be recorded and the user may decide himself at a later time, whether to use all or only some of the signals received from the light receivers. By these means, one receiver measurement may be considered as the most accurate signal to be used as a measure for the ocular light exposure.

Receiver coverage may be determined, if a ratio of light intensities of light received by the light receivers exceeds or falls below a certain value. In other words, receiver coverage may be determined, if light intensities of the light receivers differ by more than a predetermined factor. For instance, if the light intensity received by a first light receiver is a third (or three times) of the light intensity received by a second light receiver, receiver coverage may be determined. Hence, the ratio of the signals of the light receivers may serve as an indicator of receiver coverage or malfunctioning of a light receiver. Of course, the light exposure sensing system may be configured to inform the user about receiver coverage, e.g. by an optical or audible alarm signal. When receiver coverage occurs, the effective illuminance is preferably derived from other receiver signals neglecting the signal of the covered light receiver. Receiver coverage may be determined, when a signal falls below a certain threshold (<30 lux), and/or when a signal of one of the light receivers differs from the other by more than 50% (for these conditions the second light receiver may be deemed to be sleeve covered).

According to a further embodiment of the present invention, a contribution of daylight and artificial light is determined based on the received light data of the light receivers. For this, preferably a ratio of the received light intensities is used. Here, an assumption may be used, wherein a contribution of natural light is approximately the same on both, the light receiver being closer to a vertical orientation and the light receiver being closer to a horizontal orientation, while in electrical lighting conditions there is relatively little natural daylight and the contribution of electrical light in vertical orientation is typically half, or even less (down to 20%), of the contribution of electrical light in the horizontal orientation. With the illuminance ratio of vertical to horizontal illuminance for the electrical light being f, where f may have a value between 0.5 and 0.2 (preferably ca. 0.4)

the equation reads, with X referring to natural daylight contribution and Y to electrical light contribution, S1 denoting the higher signal, i.e. closer to a horizontal orientation, and S2 the lower signal, i.e. closer to a vertical orientation:

$$S1=X+Y$$

$$S2=X+fY$$

$$X/Y=\{(1/f)*S2-S1\}/\{(1/f)*(S1-S2)\}$$

Preferably, a ratio of daylight to artificial light may be assumed as the ratio between the difference of twice of the light intensity received by the light receiver closer to the vertical orientation and the light intensity received by the light receiver closer to the horizontal orientation and twice of the difference between the light intensity of the light receiver closer to the horizontal orientation and the light intensity of the light receiver closer to the vertical orientation: $X/Y=(2*S2-S1)/(2*S1-2*S2)$.

Furthermore, an orientation of the wearable device may be determined based on the light intensities received from the light receivers. For instance, it may be assumed that the light receiver receiving the higher light intensity is closer to a horizontal orientation, i.e. measures the horizontal illuminance.

Preferably, an orientation of the wearable device and/or a contribution of daylight to the illuminance may only be determined based on the light intensities of the light receiver pair, if the light intensities differ from each other by more than a predetermined threshold value and/or only if no receiver coverage is determined. By these means, artifacts resulting from receiver coverage and/or insufficient differences between the received light intensities can be avoided. For instance, outside, light exposure is rather homogenous and will result in similar light exposure for both receiving directions, so that a determination of a contribution of natural light or of an orientation may not be meaningful.

According to another aspect of the present invention, a method is provided for sensing ambient light intensity using a light exposure sensing system according to any of the above-described examples. Thus, the method for sensing light exposure of a user using at least two light receivers configured to receive light from different directions arranged on at least one wearable device includes the steps of receiving light by the light receivers from the different directions, preferably from orthogonal directions, and determining a directional illuminance based on the light data of the light received from the different directions. At least one of the light receiving directions may be not horizontal. Preferably, the determination of the illuminance uses an average or a ratio of the received light intensities. By these means, a directional illuminance of the user, such as a vertical illuminance, can be assessed.

According to the present invention, accurate ambulatory measurements of a light exposure of a user, in particular a vertical light exposure on the eye of a user can be assessed, which is of great interest for general lighting applications. For instance, this allows for services or propositions that enhance well-being by monitoring a realization of a percentage of a healthy daylight dose for a single user. This may be used as a feedback parameter to control general lighting systems, so that the illuminance automatically meets the biological light exposure needs of a user within 24 hours of a day.

The invention is also directed to a computer program provided for carrying out a method according to any one of the above-described embodiments of the invention. This computer program can be stored by the manufacturer within a memory of a light exposure sensing system or of a lighting control system, as described herein, to carry out the light exposure sensing procedure or the light controlling. A suitable storing medium can be provided to store such a computer program.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
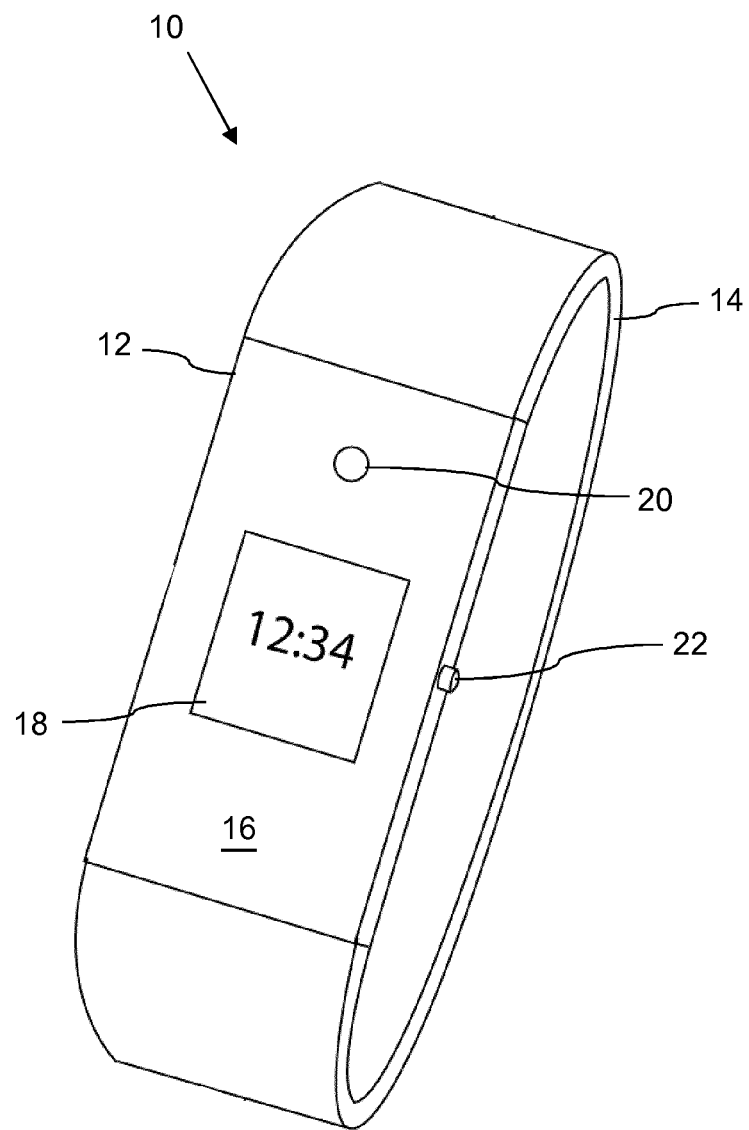
FIG. 1 is a perspective view of one embodiment of a wearable device of a light exposure sensing system according to the present invention.

FIG. 1 shows a wrist-worn device 10 of a light exposure sensing system 100 according to the present invention for sensing the ambient light intensity in the environment of a user (not shown) wearing this device 10. Generally, the wrist-worn device 10 may comprise an operation module 12 in the shape of a flat rectangular or circular box, and a flexible wristband 14 that is attached with its ends to opposite sides of the operation module 12. The inner diameter of the wristband 14 is dimensioned such that the wrist-worn device 10 can comfortably be worn on the wrist of a user. For putting on the device 10, the wristband 14 may have a certain elasticity to be widened, or an opening and closing mechanism (not shown in the Figures) may be provided at the wristband 14. Generally, the operation module 12 and the wristband 14 may be formed similar to a common wristwatch. On the top surface 16 of the operation module 12, a display unit 18 may be provided for displaying status information of the device 10 or any other information, like, for example, the daytime, date and so on. Of course, instead of a wrist-worn device, also the device 10 may also be configured as a head worn device, e.g. similar to a headlamp, or as an attachable device, such as a broche. Also, more than one device 10 may be included in the system 100, each having at least one light receiver. In this case, the devices 10 may communicate with each other wire based or wireless in order to exchange data.

Furthermore, the device 10 includes a front light receiver 20 and a lateral light receiver 22, which are arranged such that they can receive light mainly from the front or from the lateral side, respectively. Thus, the axis or direction of main sensitivity of the front light receiver 20 is directed as a normal to the front surface 16 of the device 16, and the axis or direction of main sensitivity of the lateral light receiver 22 is directed in plane or parallel to the plane of the front surface 16, i.e. perpendicular to the axis of the front light receiver 20. By these means, the device 10 can receive light from perpendicular or orthogonal directions.

Figure 2:
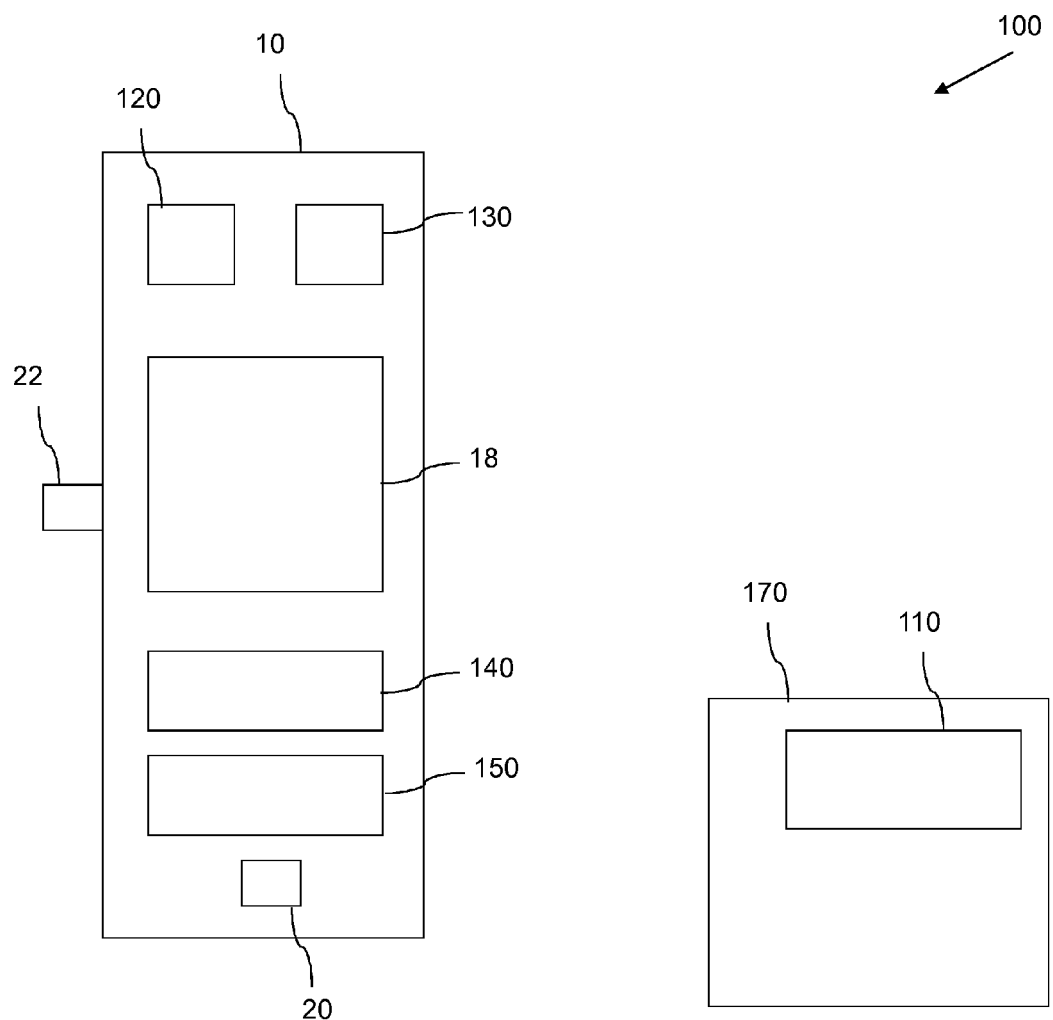
FIG. 2 is a block diagram of components of a light exposure sensing system according to one embodiment of the present invention.

In a further embodiment of a light exposure sensing system 100 shown in FIG. 2, the operation module 12 is formed as a housing that receives several components, e.g. a storage unit 140, a display unit 18, an orientation unit 130, an activity measuring unit 120 for sensing body parameters of the user and/or a communication unit 150 for transmitting and receiving data using wireless and/or wire-based transmission. Thus, the device can measure both activity or body parameters and light exposure, i.e. illuminance. Activity parameters measured by the activity measuring unit 120 include at least some of heart rate, body temperature, blood oxygen saturation, blood pressure etc. The orientation unit 130 for determining a spatial orientation of the device 10 can be realized as an accelerometer or the like, so that the 3-dimensional position of the device 10, and thus also the positions of the light receivers 20, 22 of the device 10 can be determined. This information can be used by the control unit 110 for weighting received data based on the orientation of the device 10. In case that more than one device 10 is included in the system 100, the devices 10 may communicate wire based or wireless with the control unit 110 for data exchange.

The control unit 110 can include an integrated electronic circuit for processing electric signals and may be either included in the operation module 12 of the device 10 or in a separate unit of the light exposure sensing system 100, such as a docking station 170, as shown in FIG. 2. In the latter case, the device 10 is configured to exchange data with the control unit 110 via wire-based or wireless communication using the communication unit 150. The docking station 170 can be further configured for charging or calibrating the device 10. Moreover, the control unit 110 can also include some memory means. Alternatively or additionally, the storage unit 140 may be included in the wearable device 10.

Figure 3:
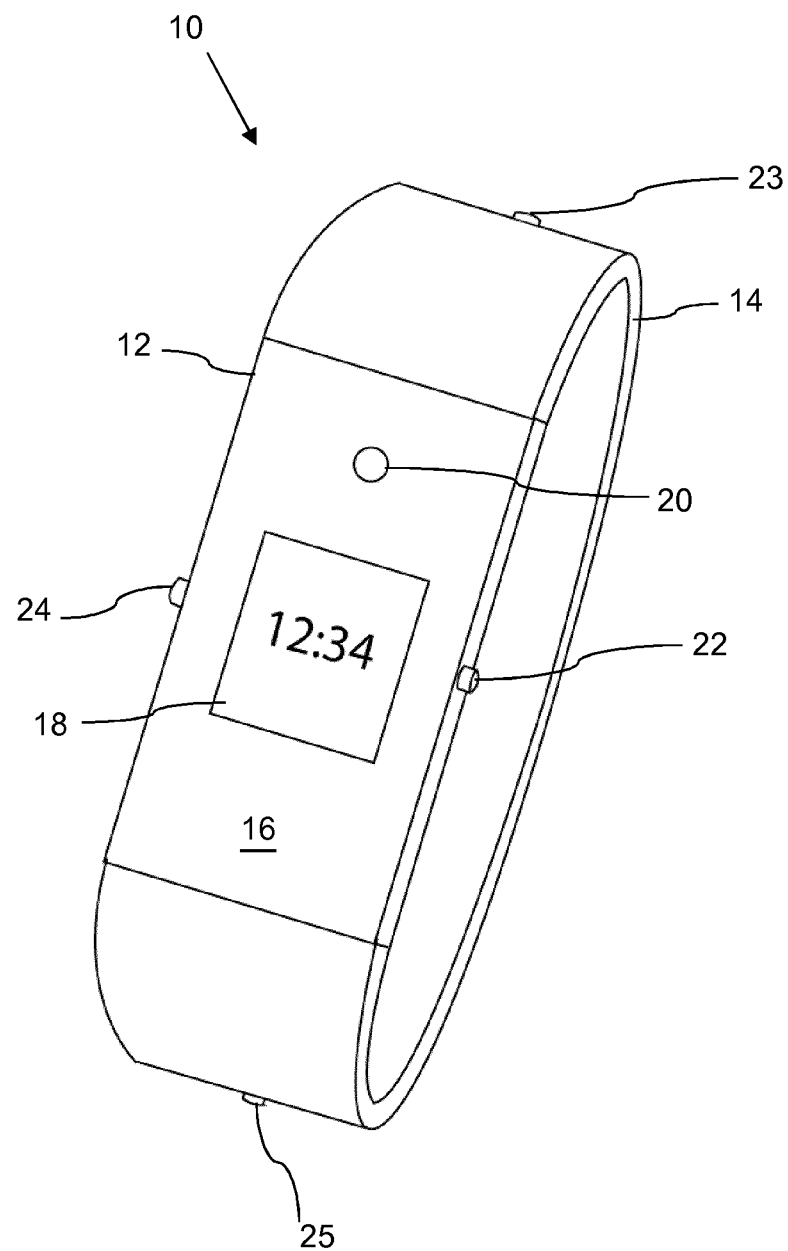
FIG. 3 is a perspective view of another embodiment of a wrist-worn device according to the present invention.
Figure 4:
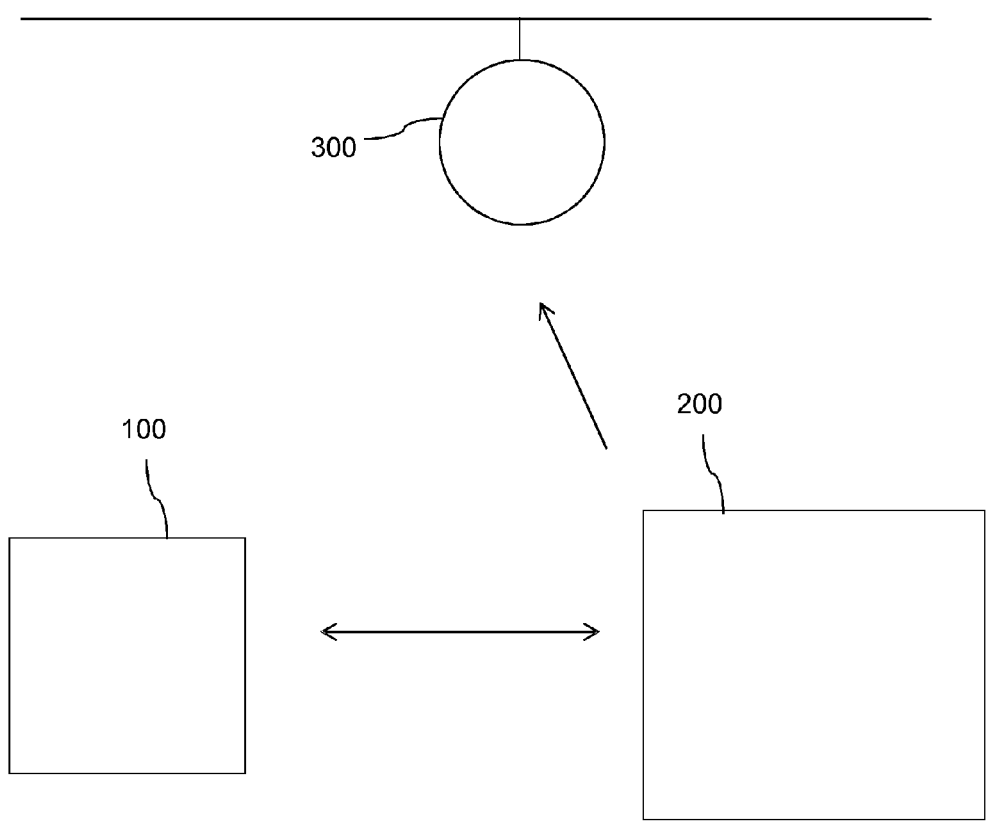
FIG. 4 is a block diagram of a lighting control system according to a further embodiment of the present invention.

In FIG. 3, a further embodiment of a wearable device 10 shown having a plurality of lateral receivers 22, 23, 24, 25 arranged in orthogonal orientations to each other. In this case, the control unit 110 may be configured to arrange the light receivers 20, 22, 23, 24 and 25 in pairs with orthogonal orientation. For instance, the front light receiver 20 and any of the lateral light receivers 22, 23, 24 and 25 could represent such a pair of orthogonal receivers. The front light receiver 20 can also be paired with more than one of the lateral light receivers 22, 23, 24 and 25. Although in FIG. 3, the lateral light receivers 23 and 25 are shown to be located at the wristband 14, they can also be located at side surfaces of the operation module 12, as long as they are orientated towards an upper and lower direction perpendicular to the orientation of the front light receiver 20 and the other lateral light receivers 22 and 24. The control unit 110 can then select data from a certain receiver pair for determining the illuminance, e.g. based on orientation, measured light intensities or signal quality.

The control unit 110 receives activity data from the activity measuring unit 120, orientation data from the orientation unit 130, a charging level of the device 10, light intensity signals from the light receivers 20, 22, 23, 24, 25 or the like. In order to determine a vertical illuminance on the eye of a user, the control unit 110 combines the signals of at least one pair of orthogonal light receivers, e.g. of light receivers 20 and 22. It is known that even when an actigraphic wristworn device, like device 10, is worn over the sleeve by a user, its light receiver reading has a correlation of less than 0.5 with the vertical illuminance on the eye. However, according to one embodiment of the present invention, light intensities measured in two different orthogonal directions are combined for obtaining a light exposure parameter as a measure for vertical illuminance at the eye position. By this, a better correlation with the ocular illuminance can be achieved, compared to a device having only one light sensing direction. The control unit 110 can obtain the light exposure parameter using a ratio of the light intensities received from the orthogonal light receiver pair or by taking the average therefrom. The control unit 110 can also weight the light intensities of one receiver pair and also light intensities received from further receiver pairs based, for instance, on signal quality, estimated orientation of the respective light receivers or using preset parameters. In one example, only the light intensity with the higher value among the intensities received from one receiver pair may be considered for determining the vertical illuminance. This may be useful, if receiver coverage for this light receiver pair is detected.

In one embodiment, the processing by the control unit 110 includes a receiver coverage adjusting algorithm, wherein it is determined whether a light receiver 20, 22, 23, 24, 25 is covered by clothing or the like. For this, a difference between light intensities received from one light receiver pair is evaluated, e.g. using the ratio of the light intensities. For instance, the ratio of the light intensity signal S1 of the front light receiver 20 and the light intensity signal S2 of the lateral light receiver 22 is determined. If the ratio S1/S2 is equal or less than 0.33, it is indicative of receiver coverage. Therefore, if a ratio between the ratio of light intensities received from one orthogonal light receiver pair falls below a lower threshold value, e.g. 0.33, or likewise exceeds an upper threshold value, e.g. 3, receiver coverage is determined.

In case of receiver coverage, the readout of the device 10 and the software platform in the control unit 110 can consider only the higher intensity values measured by the lateral light receiver 22 as a measure of the vertical ocular illuminance. Alternatively, the user might be given the chance to accept or deny such an action. Also, the user may be informed about the receiver coverage by an acoustic alarm or the like. Of course, as mentioned above, the control unit 110 may also be located in the device 10 itself, so that the light information could be combined in the device 10. In this case, the algorithm of the control unit 110 integrated in the device 10 could take the input of only the lateral light receiver 22 as the value to store and neglect the input from the front light receiver 20.

In a further embodiment that can be combined with any of the previously described embodiments, the control unit 110 includes an algorithm for discriminating electric and daylight contributions in the illuminance experienced by a user. Since outdoor light exposure is more homogenous and will result in a similar light exposure for horizontal and vertical light receiving orientations, daylight should always contribute roughly the same amount to both light receivers 20, 22 of an orthogonal receiver pair. In contrast, indoor or artificial light is more heterogeneous and should contribute roughly to the vertical illuminance half of the horizontal illuminance. Therefore, the signal perceived by the light receivers 20, 22 of an orthogonal light receiver pair should be different, wherein the light receiver 20, 22 closer to a horizontal orientation generally measures indoors the higher intensity values. Hence, the signals of two orthogonally sensing light receivers can be used to separate daylight and electric light contributions using the following assumption: daylight contribution X is the same on both light receivers 20, 22 of an orthogonal light receiver pair, i.e. the daylight contribution X is the same in horizontal and vertical orientation. Electric light contribution Y, in contrast, is 1 in horizontal orientation of the light receiver and typically 0.5 or even less in the vertical orientation, e.g. between 0.2 and 0.4 in vertical orientation. Possibly, one could take a mean value using 0.35-0.4 instead of 0.5. Hence, when measuring light intensities by light receiver 20 receiving light in horizontal orientation and lateral light receiver 22 receiving light in vertical orientation, front light receiver 20 measures signal S1 and lateral light receiver 22 measures signal S2. With the illuminance ratio of vertical to horizontal illuminance within the electrical light being denoted f (f may have a value between 0.5 and 0.2, preferably between 0.35 and 0.4), X referring to natural daylight contribution and Y to electrical light contribution, the following relations can be used:

$$S1=X+Y, \text{ and} \quad (1)$$

$$S2=X+fY. \quad (2)$$

From these relations, the ratio of daylight and electric light X/Y can be obtained, with:

$$X/Y=\{(1/f)*S2-S1\}/\{(1/f)*(S1-S2)\}. \quad (3)$$

That is, for f=0.5, X/Y=(2*S2−S1)/(2*S1−2*S2). In these relations, signal S1 originates always from the light receiver closer to a horizontal orientation.

In addition to determining the contribution of daylight, the light intensities received by an orthogonal light receiver pair can also be used for determining the orientation of the wearable device 10. Since the light receiver 20 receiving the higher intensity signal among the two light receivers 20, 22 of one light receiver pair should be closer to a horizontal orientation, the control unit 110 can estimate the position of the device 10 by identifying the light receiver 20 providing the higher light intensity value as horizontal light receiver. Of course, the algorithm for determining electric and daylight contribution only works well, if no receiver coverage occurs and if the values of signals S1 and S2 are not too close. If the values S1 and S2 are too close, i.e. R=1, the user is probably outdoors, or in a very diffuse indoor environment. Therefore, the control unit 110 preferably only applies the algorithm for determining natural and artificial light contribution or for determining the orientation of the device 10, if the ratio R=S1/S2 meets:1.1<R<4 with S1 being defined as the signal from the light receiver receiving the highest light intensity, i.e. the light receiver closer to a horizontal orientation. Therefore: S1/S2>=1. When R is between 1 and 1.1 or when R>4, above relations (1) to (3) do not apply. If R>4, then most of the light comes from one direction, indicating that the majority of the light is coming from electrical lighting with very little daylight contribution. In this case, the daylight contribution can be deemed to be negligible small. It can be derived from the S2 signal, assuming the relations $$S2=X \text{ and } S1=X+Y \text{ with } Y>>X. \quad (4)$$

This value X as derived from S2 may then be the best representation of the vertical illuminance. When the previous conditions apply and S2=X is very low, say less then 20 lux, then the light receiver providing the signal S2 is probably covered by a sleeve. In that case, S1 may yield the best representation of the vertical illuminance.

In a further embodiment, the wrist worn device 10 includes the orientation unit 130, e.g. an accelerometer or a 3D-motion sensing device measuring orientation with respect to gravity or the Earth magnetic field. Generally, orientation information can be used in the algorithm for determining vertical illuminance, natural light contribution or electric light contribution, for giving the light receiver having an orientation closer to the vertical orientation more weight, when combining the light intensity signals of one orthogonal light receiver pair. In this case, the combining algorithm may merge the two sensing directions into one parameter describing the ocular vertical illuminance, wherein the weighting factors for the two light sensing directions can have values between 0 and 1. When the light sensing direction of a light receiver exactly coincides with the ocular viewing direction, its weighting factor may be set to 1 by the control unit 110. Likewise, when the light sensing direction of a light receiver is orthogonal to the viewing direction, its weighting factor may be set to 0.

According to a further embodiment of the present invention, the light exposure sensing system 100 according to anyone of the above-described embodiments may be combined with a general lighting system. For this, the device 10 or the control unit 110 may communicate with a central control unit 200 of a lighting control system for controlling the lighting system 300, to indicate that a user needs more or less light at a given time for achieving an optimal stimulation needed for a stable, well-entrained and healthy sleep and wake rhythm. The device output can also be used to give feedback to the user about a healthy light exposure, either by indicators displayed or output by the device 10 or via web services. The central control unit 200 can then control one or more lighting systems 300, the lighting system being e.g. a large illumination system or a single lamp, a goLITE or energy light or the like, based on the data received from the light exposure sensing system 100. By these means, it can be assured that the light exposure of a user automatically meets the biological light exposure within 24 hours.

In the above-described examples, sensors are used as light receivers 20, 22, 23, 24, 25 to transform light into an electric signal that can be further processed and/or stored by the control unit 110. In one embodiment, the sensors 20, 22, 23, 24, 25 are represented by opto-sensitive electronic components. However, it is possible to arrange other kinds of light receivers 20, 22, 23, 24, 25 instead of sensors, that also have a main axis of maximum receptivity for light, in form of optical elements that collect light and further supply the collected light via light guiding means towards a common sensor that is included in the device 10, so that the electric signal is generated by this common sensor. It is also possible that the light receivers 20, 22, 23, 24, 25 (i.e. sensors or any other kinds of light collecting optical elements) are provided to receive light of one or a plurality of spectral ranges, for example, within the visible light spectrum or in the infrared or ultraviolet spectral area. Thus, the control unit 110 may process the signals of the light receivers 20, 22, 23, 24, 25 based on one selected spectral range.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A light exposure sensing system for sensing light exposure of a user, comprising:
   at least one wearable device;
   at least two light receivers oriented towards different directions orthogonal to each other and configured to receive light from the different directions, the light receivers being arranged on the at least one wearable device, and
   a control unit configured to determine light intensities received from the at least two light receivers,
   wherein the control unit is further configured to determine a ratio of daylight to artificial light (X/Y) based on the light intensities received from the at least two light receivers and based on the relation $$X/Y=\{(1/f)*S2-S1\}/\{(1/f)*(S1-S2)\},$$

wherein a highest light intensity of the light intensities received from the at least two light receivers is denoted as S1, a lowest light intensity of the light intensities received from the at least two light receivers is denoted as S2, and f is an illuminance ratio of vertical to horizontal illuminance from the artificial light.

2. The light exposure sensing system according to claim 1, wherein the control unit is further configured to determine a directional illuminance of the user using a ratio of the light intensities received from the at least two light receivers, or an average or a weighted average of the light intensities received from the at least two light receivers.

3. The light exposure sensing system according to claim 2, wherein the at least two light receivers are grouped in a plurality of pairs and the control unit is configured to select a pair of light receivers from the plurality of pairs for determining the directional illuminance.

4. The light exposure sensing system according to claim 1, wherein the light intensities are weighted differently based on an orientation of the wearable device and/or of the respective light receivers.

5. The light exposure sensing system according to claim 1, wherein the control unit is configured to determine receiver coverage, if the light intensities received from the at least two light receivers differ from each other more than a predetermined factor and/or at least one of the light intensities is below a certain threshold value.

6. The light exposure sensing system according to claim 1, wherein the light receivers have the same spectral sensitivity.

7. The light exposure sensing system according to claim 1, wherein an orientation of the wearable device is determined by assuming that the light receiver receiving the highest light intensity is closer to a horizontal orientation than the light receiver receiving the lowest light intensity.

8. The light exposure sensing system according to claim 1, wherein an orientation of the wearable device and/or the ratio of daylight to artificial light is determined based on the light intensities received from the at least two light receivers only if a ratio of the light intensities differs from 1 more than a predetermined threshold value and/or if no receiver coverage is determined.

9. The light exposure sensing system according to claim 1, wherein the wearable device and/or the system further includes at least one of:
   an activity measuring unit for measuring body parameters of the user;
   an orientation unit for determining an orientation of the wearable device and/or of at least one of the light receivers;
   a storage unit for storing data;
   a display unit for displaying data; and
   a communication unit for data exchange.

10. A lighting control system for ensuring a predetermined light exposure, comprising:
    a light exposure sensing system including:
      at least one wearable device;
      at least two light receivers oriented towards different directions orthogonal to each other and configured to receive light from the different directions, the light receivers being arranged on the at least one wearable device, and
      a control unit configured to determine light intensities received from the at least two light receivers,
      wherein the control unit is further configured to determine a ratio of daylight to artificial light (X/Y) based on the light intensities received from the at least two light receivers and based on the relation $$X/Y=\{(1/f)*S2-S1\}/\{(1/f)*(S1-S2)\},$$

wherein a highest light intensity of the light intensities received from the at least two light receivers is denoted as S1, a lowest light intensity of the light intensities received from the at least two light receivers is denoted as S2, and f is an illuminance ratio of vertical to horizontal illuminance from the artificial light, and wherein the control unit is further configured to determine a directional illuminance of a user using a ratio of the light intensities received from the at least two light receivers, or an average or a weighted average of the light intensities received from the at least two light receivers;
    at least one lighting system; and
    a central control unit, configured to use the determined directional illuminance, which is received from the light exposure sensing system, as a feedback parameter to control the at least one lighting system.

11. A method for sensing light exposure of a user using at least two light receivers arranged in different directions on at least one wearable device, the method comprising:
    receiving light from the different directions by the at least two light receivers,
    wherein a ratio of daylight to artificial light is determined based on the light intensities of the light received from the different directions by the at least two light receivers and based on the relation $$X/Y=\{(1/f)*S2-S1\}/\{(1/f)*(S1-S2)\},$$

wherein the highest light intensity of the light intensities of the light received by the at least two light receivers is denoted as S1, the lowest light intensity of the light intensities of the light received by the at least two light receivers is denoted as S2, and f is an illuminance ratio of vertical to horizontal illuminance from the artificial light.

* * * * *